(12) United States Patent
Schoerken et al.

(10) Patent No.: US 7,604,966 B2
(45) Date of Patent: Oct. 20, 2009

(54) PROCESS FOR THE PRODUCTION OF STRUCTURED LIPID MIXTURES

(75) Inventors: Ulrich Schoerken, Duesseldorf (DE); Doris Bell, Duesseldorf (DE); Peter Horlacher, Bellenberg (DE); Diana Stuhlmann, Duesseldorf (DE); Carolin Meyer, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 8 days.

(21) Appl. No.: 11/554,799

(22) Filed: Oct. 31, 2006

(65) Prior Publication Data

US 2007/0111292 A1   May 17, 2007

(30) Foreign Application Priority Data

Nov. 3, 2005   (DE) ........................ 10 2005 052 442

(51) Int. Cl.
   C12P 7/64   (2006.01)
(52) U.S. Cl. ....................................... 435/134
(58) Field of Classification Search ................ 435/134
   See application file for complete search history.

(56) References Cited

U.S. PATENT DOCUMENTS

2005/0215641 A1   9/2005   Saebo et al.
2007/0281993 A1*  12/2007  Rozen et al. ................. 514/458

FOREIGN PATENT DOCUMENTS

WO   WO 03/043972   5/2003

OTHER PUBLICATIONS

Torres et al., Enyzme and Microbial Technology, . vol. 32, 2003, pp. 49-58.*
Raes et al. Journal of Nutrition, vol. 132, pp. 182-189, 2002.*
Torres et al., JOAOCS, vo. 78, No. 11, pp. 2001-2011, 2001.*
Gracia et al., Bioteechnology & Bioengineering, vol. 70, No. 5, pp. 587-591, 2000.*
Torres et al., "Preparation of purified acylglycerols of eicosapentaenoic acid and docosahexaenoic acid and their re-esterification with conjugated Llnoleic acid," Enzyme and Microbial Technology, 2003, pp. 49-58. XP-002419907.
Raes, et al., "The Deposition of Conjugated Linoleic Acids in Eggs of Laying Hens Fed Diets Varying in Fat Level and Fatty Acid Profile," Journal of Nutrition, 2002, pp. 182-189. XP-002419908.

Torres et al., "Esterification of Glycerol with Conjugated Linoleic Acid and Long-Chain Fatty Acids from Fish Oil," Journal of American Oil Chemists' Society, AOCS Press, 2001, pp. 1093-1098. XP-001073021.
Garcia et al., "Synthesis of Glycerides Containing n-3 Fatty Acids and Conjugated Linoleic Acid by Solvent-free Acidolysis of Fish Oil," Biotechnology and Bioengineering, 2000, pp. 587-591. XP-002419909.
Garcia et al., "Interesterification (Acidolysis) of Butterfat with Conjugated Linoleic Acid in a Batch Reactor," Journal of Dairy Science, Am. Dairy Science Assoc., 2000, pp. 371-377. XP-000926920.
Chilliard eta?., "Ruminant milk fat plasticity: nutritional control of saturated, polyunsaturated, trans and conjugated fatty acids," Ann. Zootech., 2000, pp. 181-205. XP-002419910.
Hillbrick et al., "Milkfat characteristics and functionality: opportunities for Improvement," Australian Journal of Dairy Technology, Dairy Industry Assoc. Of Australia, 2002, pp. 45-51. XP-001102103.
Osborn etal., "Structured Lipids—Novel Fats with Medical, Nutraceutical, and Food Applications," Comprehensive Reviews in Food Science and Food Safety, vol. 3, 2002, pp. 110-120. XP-002419911.

* cited by examiner

*Primary Examiner*—Deborah D Carr

(57) ABSTRACT

The invention relates to structured lipid mixtures corresponding to formula (I):

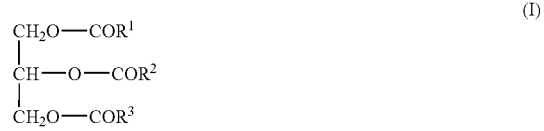

characterized in that $R^1CO$, $R^2CO$ and $R^3CO$ independently of one another represent
(i) linear saturated acyl groups containing 6 to 12 carbon atoms or
(ii) the acyl group of conjugated linoleic acid (CLA) and/or an omega-3 or omega-6 fatty acid (OF),
with the proviso that the quantity of CLA acyl groups amounts to 3 to 50 mol-% and the quantity of OF acyl groups to 5 to 25 mol-%, based on the quantity of acyl groups. The mixtures are preferably made by subjecting a mixture of component (a) a medium-chain triglyceride; and component (b) a CLA, an (OF), a TG-CLA (TG-OF) or a mixture thereof to enzymatic transesterification in the presence of a vegetable, marine or microbial oil.

21 Claims, No Drawings

PROCESS FOR THE PRODUCTION OF STRUCTURED LIPID MIXTURES

CROSS-REFERENCE TO RELATED APPLICATIONS

This application claims priority under 35 U.S.C. §119 from German Patent Application No. 10 2005 052 442.7, filed Nov. 3, 2005.

STATEMENT REGARDING FEDERALLY SPONSORED RESEARCH OR DEVELOPMENT

The subject matter of this application does not concern federally sponsored research or development.

BACKGROUND OF THE INVENTION

This invention relates generally to food additives and supplements and, more particularly, to structured lipid mixtures, to a process for their production and to their use in human nutrition, more particularly for controlling weight.

In recent years, special triglycerides with C chain lengths of 6 to 10 carbon atoms—known as medium-chain triglycerides (MCTs)—have acquired growing significance because they reduce the uptake of fats in human nutrition and increase both the burning of fat and the metabolization rate. In practical application, too, structured lipids have many advantages over "normal" natural lipids, albeit dependent to a large extent on the particular application. Typical examples are

- establishment of optimal physical properties (for example in margarine, confectionery fats, CBE)
- creation of a special triglyceride molecule (for example in the case of OPO triglycerides for infant nutrition)
- highly concentrated TGs for the administration of active fatty acids (for example triglycerides based on conjugated linoleic acid, docosahexaene carboxylic acid or eicosapentaenoic acid)
- rapid energy supply (MCTs and lipids containing medium-chain fatty acids)
- reduced-calorie lipids (for example salatrim, caprenin) and dietetic oils with a structure-based effect (for example Enova oil, MCT-based lipids)
- lipids with accelerated absorption (shown for lipids with medium-chain fatty acids)

For the reasons mentioned, it has been consistently proposed in the literature to replace conventional "less healthy" edible oils, for example sunflower oil, olive oil or thistle oil, with "particularly healthy" MCTs. However, this has proved to be extremely difficult in practice because, to benefit from the advantageous properties of MCTs, an average adult would have to take an average dose of 20 g/day. However, this is already of the order of the average daily intake of edible oils, i.e. there would then be no room for more oils.

The complex problem addressed by the present invention was to provide an oil for daily use

- which would have a healthy composition according to recommendations from nutritionists in regard to
- a sufficient percentage content of essential fatty acids such as, for example, conjugated linoleic acid (CLA) or omega-3 or omega-6 fatty acids,
- a ω-6/Ω-3 ratio in the oil of 5:1 to 1:1.
- a high percentage content of oleic acid of more than 20 mol-% and
- a low percentage content of saturated and trans fatty acids (excluding the essential fatty acids), which, at the same time, would have an active character in relation to reducing percentage body fat promoted by

- a high percentage content of directly metabolizable medium-chain fatty acids
- a recommended dose of effective CLA isomers
- and which would be absorbed particularly well through a high percentage content of structured triglycerides with one or two medium-chain acyl groups in the oil.

Another requirement to be satisfied by the products to be provided by the invention would be that they would be similar to known edible oils in their physicochemical behavior, for example in their cloud point, smoke point, oxidation stability and viscosity. Another problem addressed by the present invention was to produce the structured lipid in a sensory quality comparable with that of the usual edible oils.

A final problem addressed by the invention was to provide "gentle" production processes for the structured lipids which would enable high-quality products to be produced.

BRIEF SUMMARY OF THE INVENTION

The present invention relates to structured lipid mixtures corresponding to formula (I):

characterized in that $R^1CO$, $R^2CO$ and $R^3CO$ independently of one another represent (i) linear saturated acyl groups containing 6 to 12 carbon atoms or (ii) the acyl group of conjugated linoleic acid (CLA) and/or an omega-3 or omega-6 fatty acid (OF), with the proviso that the quantity of CLA acyl groups amounts to 3 to 50 mol-% and preferably to 5 to 15 mol-% and/or the quantity of OF acyl groups amounts to 5 to 25 mol-% and preferably to 7 to 15 mol-%, based on the quantity of all acyl groups.

The products corresponding to formula (I) in which the fatty acids are statistically distributed in the three possible positions ("random products") include the species of formula (I) in which $R^1CO$ and $R^3CO$ represent linear saturated acyl groups containing 6 to 12 carbon atoms and $R^2CO$ represents the acyl group of conjugated linoleic acid (CLA) and/or an omega-3 or omega-6 fatty acid (OF) and which are referred to hereinafter as being of the "ABA type".

With the desired properties in mind, lipid mixtures of formula (I) distinguished by the following structural features—either individually or in combination—have proved to be particularly preferable:

- a content of triglycerides derived either from one medium-chain and two long-chain fatty acids or from two medium-chain and one long-chain fatty acid of at least 60 mol-%.
- a content of more than 20 mol-% oleic acid, based on the content of long-chain fatty acids, and a content of less than 20 mol-% saturated $C_{12-22}$ fatty acids and a content of less than 2 mol-% unsaturated trans fatty acids, excluding CLA and OF.

a content of at least 90 mol-% of the CLA bound in the molecule in the form of the 9-cis, 11-trans isomer or the 10-trans, 12-cis isomer or mixtures of these two isomers.

a content of acyl groups which—where they are derived from omega-3 or omega-6 fatty acids—are present in a ω-6/ω-3 ratio of 5:1 to 1:1.

The invention also provides processes for the production of the structured lipid mixtures of formula (I). Other aspects of the invention are described in the embodiments of the invention set out below.

DETAILED DESCRIPTION OF THE INVENTION

It has surprisingly been found that the structured lipids according to the invention most effectively satisfy the desired complex requirement profile and, besides their favorable nutrition-physiological properties, show in particular improved degradability through improved emulsifiability and, hence, have improved accessibility to digestion lipases in relation, for example, to pure CLA triglyceride, which improves the availability of CLA. The improved availability of the active fatty acids is accompanied by additional advantages in the physical product properties. Thus, lipids were obtained which have a significantly improved smoke point by up to 25° C. in relation to corresponding mixtures of long-chain and medium-chain triglycerides and which show distinctly increased oxidation stability in relation to the vegetable oils used and to the CLA-TG. In addition, the structured lipids according to the invention have improved sensory properties both in regard to odor and in relation to taste by comparison with the vegetable oils used in their synthesis.

Transesterification and Esterification

It is pointed out by way of precaution at this juncture that the expression "conjugated linoleic acid" is intended to encompass typical technical mixtures of position isomers which have different cis/trans ratios and which may also contain small amounts of conventional linoleic acid and—from the production process—other fatty acids. CLA is normally obtained by base-catalyzed isomerization of thistle oil or corresponding alkyl esters and subsequent enzymatic hydrolysis. It has proved to be of advantage in this regard if the CLA meets a certain specification, according to which the acyl group contains at least 30% by weight t10, c12 isomers, at least 30% by weight c9, t11 isomers and, in all, less than 1% by weight 8,10-, 11,13- and t,t-isomers. The same applies to the triglyceride based on conjugated linoleic acid (CLA-TG). Corresponding products are commercially available, for example, under the names of Tonalin® CLA-80 and Tonalin® CLA-TG. In addition, for the production of pharmaceutical products, it has proved to be particularly advantageous if the CLA consists purely of c10, t12 or t9, c11 isomers.

Omega-3 or omega-6 fatty acids typically contain 20 to 28 carbon atoms and 4 to 6 double bonds. They may be obtained, for example, from marine sources, particularly from the various fish oils, or by fermentation, for example using microalgae. The most well-known representatives are DHA (docohexaenoic acid) and EPA (eicosapentaenoic acid).

Numerous MCTs are available commercially, for example, Myritol® 312, Myritol® 318, Delios® C, Delios® S, and Delios® V (all from Cognis Deutschland GmbH & Co. KG).

The present invention also relates to a first process for the production of structured lipid mixtures corresponding to formula (I):

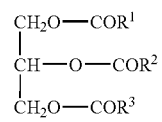

in which $R^1CO$, $R^2CO$ and $R^3CO$ independently of one another represent (i) linear saturated acyl groups containing 6 to 12 carbon atoms or (ii) the acyl group of conjugated linoleic acid (CLA) and/or an omega-3 or omega-6 fatty acid (OF), with the proviso that the quantity of CLA acyl groups amounts to 3 to 50 mol-% and preferably to 5 to 15 mol-% and/or the quantity of OF acyl groups amounts to 5 to 25 mol-% and preferably to 7 to 15 mol-%, based on the quantity of acyl groups, characterized in that (a) so-called medium-chain triglycerides (MCTs) corresponding to formula (II):

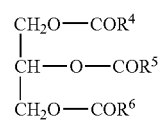

where $R^4CO$, $R^5CO$ and $R^6CO$ independently of one another stand for a linear saturated acyl group containing 6 to 12 carbon atoms, and (b) conjugated linoleic acid (CLA) and/or omega-3 fatty acids (OF) and/or omega-6 fatty acids (OF) and/or triglycerides based on conjugated linoleic acid (TG-CLA) or on omega-3 or omega-6 fatty acids (TG-OF) are subjected to enzymatic transesterification.

Besides the transesterification of MCT with CLA or CLA-TG, the new substances may also be obtained by esterification. Accordingly, the present invention also relates to a second process for the production of structured lipid mixtures corresponding to formula (I):

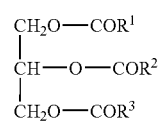

in which $R^1CO$, $R^2CO$ and $R^3CO$ independently of one another represent (i) linear saturated acyl groups containing 6 to 12 carbon atoms or (ii) the acyl group of conjugated linoleic acid (CLA) and/or an omega-3 or omega-6 fatty acid (OF), with the proviso that the quantity of CLA acyl groups amounts to 3 to 50 mol-% and preferably to 5 to 15 mol-% and/or the quantity of OF acyl groups amounts to 5 to 25 mol-% and preferably to 7 to 15 mol-%, based on the quantity of acyl groups, characterized in that (a) mixtures of fatty acids or esters of fatty acids corresponding to formula (III):

in which $R^7CO$ is a linear saturated acyl group containing 6 to 12 carbon atoms and $R^8$ is hydrogen or an alkyl group containing 1 to 4 carbon atoms, preferably methyl, and (b) conjugated linoleic acid (CLA) and/or omega-3 and/or omega-6 fatty acids are subjected to enzymatic esterification or transesterification in the presence of glycerol.

In addition, in order to incorporate the desired quantity of CLA or OF in the structured lipids, it has proved to be of advantage to use the MCTs or fatty acids on the one hand and the CLA and/or OF or their triglycerides on the other hand in a molar ratio of 1:1 to 20:1, based on the fatty acid equivalents. Typical examples in this regard are rapeseed oil, soybean oil, sunflower oil, thistle oil, olive oil, perilla oil, borage oil, linseed oil tuna oil, sardine oil, salmon oil, mackerel oil and algal oils and other microbial oils rich in polyunsaturated fatty acids. The MCTs or the fatty acids on the one hand and the oils on the other hand are generally used in a molar ratio of 5:1 to 1:5 and, more particularly, in a molar ratio of 3:1 to 1:3, based on fatty acid equivalents. The conditions under which the enzymatic reactions are carried out are known per se to the expert and—where this is not in any case sufficiently illustrated by the Examples—may be determined and established by the expert without requiring inventive activity. In particular, a reaction temperature of 20 to 70° C. and, more particularly, 40 to 60° C. and, irrespective of the reaction temperature, a reaction time of 2 to 50 and preferably 10 to 25 hours have proved to be advantageous both for the transesterification and for the esterification.

Enzymes

The choice of enzyme is critical insofar as regioselectivity on the one hand and the conversion level on the other hand can be controlled through the choice of enzyme. Basically, enzymes of the lipase or esterase type are required for the production of the structured lipids whether by transesterification or by esterification. These lipases are preferably microbial lipases and are selected from the group consisting of *Rhizomucor miehei, Thermomyces lanugenosus* and *Candida antarctica B*. In addition, it has been found to be of advantage to use lipases which are present in known manner in immobilized form.

Working Up of the Reaction Products

After the transesterification or esterification, it has proved to be of advantage to remove unreacted fatty acids, esters and monoglycerides from the reaction products by distillation, for example at temperatures below 220° C. and under pressures of less than 1 mbar. The products are then normally subjected to deodorization and/or bleaching using bleaching clay and/or active carbon. In addition, during and/or after the reaction, antioxidants approved for use in foods may be added to the mixture, for example in a concentration of 100 to 2,000 ppm.

Commercial Applications

Accordingly, the present invention also relates to the use of the new structured lipid mixtures as foods or food supplements, as a constituent of pharmaceutical preparations or animal feeds. These new products may be, for example, edible oils or dietetic oils, grilling and frying oils and the like. In addition, the lipids may be a constituent of dressings, mayonnaises, margarines, dairy products, juices, confectionery and candies and the like. The lipid mixtures may be used for transesterification with hydrogenated fats for producing lipids with adjustable solid fat contents, melting and crystallization behavior. In addition, the lipids may be made up into various supply forms, more particularly in the form of macro- or microcapsules. Another supply form are stable emulsions containing emulsifiers, such as phospholipids for example, for use in pharmaceutical preparations, more particularly for parenteral nutrition.

The lipids in general may be used for daily nutrition and are suitable for completely replacing food-grade fats. The lipids according to the invention have a sufficient content of essential fatty acids in a nutrition-physiologically advantageous ω-6/ω-3 balance. An additional benefit of the lipids lies in their active effects. Medium-chain fatty acids supply the body with rapidly available energy without putting on body weight while CLA has a positive influence on the balance between body fat and muscle. In addition, the structured lipids guarantee ready availability of the omega-3 or omega-6 fatty acids and the CLA. Accordingly, the structured lipids according to the invention are suitable for use as a dietetic oil and as an energy source in sports nutrition and for the nutrition of patients with disorders of the metabolism and also for the production of a medicament for treating such disorders.

A few selected embodiments of the present invention are listed in the following:

1. Mixture containing lipids corresponding to formula (I):

characterized in that $R^1CO$, $R^2CO$ and $R^3CO$ independently of one another are selected from the group consisting of (i) a linear saturated acyl group containing 6 to 12 carbon atoms, (ii) the acyl group of conjugated linoleic acid (CLA)

(iii) the acyl group of an omega-3 fatty acid (OF) and (iv) the acyl group of an omega-6 fatty acid (OF), with the proviso that the quantity of CLA acyl groups in the mixture amounts to 3 to 50 mol-% and the quantity of OF acyl groups in the mixture amounts to 5 to 25 mol-%, based on the quantity of all acyl groups in the mixture.

2. Mixture according to embodiment 1, characterized in that $R^1CO$ and $R^3CO$ stand for linear saturated acyl groups containing 6 to 12 carbon atoms and $R^2CO$ is the acyl group of conjugated linoleic acid (CLA) and/or an omega-3 or omega-6 fatty acid (OF) (ABA type).

3. Mixture according to embodiment 1 or 2, characterized in that it has a content of triglycerides derived either from one medium-chain and two long-chain fatty acids or from two medium-chain and one long-chain fatty acid of at least 60 mol-%.

4. Mixture according to any of embodiments 1 to 3, characterized in that it has a content of more than 20 mol-% oleic acid, based on the content of long-chain fatty acids, and a content of less than 20 mol-% saturated $C_{12\text{-}22}$ fatty acids and a content of less than 2 mol-% unsaturated trans fatty acids, excluding CLA and OF.

5. Mixture according to any of embodiments 1 to 4, characterized in that at least 90 mol-% of the CLA bound in the molecule is either the cis 9, trans 11 isomer or the 10 trans, cis 12 isomer or mixtures of these two isomers.

6. Mixture according to any of embodiments 1 to 5, characterized in that the acyl groups derived from omega-3 or omega-6 fatty acids are present in a ω-6/ω-3 ratio of 5:1 to 1:1.

7. Process for the production of the mixture according to embodiment 1, characterized in that (a) so-called medium-chain triglycerides (MCTs) corresponding to formula (II):

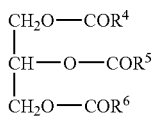

where $R^4CO$, $R^5CO$ and $R^6CO$ independently of one another stand for a linear saturated acyl group containing 6 to 12 carbon atoms, and (b) conjugated linoleic acid (CLA) and/or omega-3 fatty acids (OF) and/or omega-6 fatty acids (OF) and/or triglycerides based on conjugated linoleic acid (TG-CLA) and/or triglycerides based on omega-3 or omega-6 fatty acids (TG-OF)

are subjected to enzymatic transesterification.

8. Process for the production of the mixture according to embodiment 1, characterized in that (a) mixtures of fatty acids or esters of fatty acids corresponding to formula (III):

$$R^7COOR^8 \qquad (III)$$

in which $R^7CO$ is a linear saturated acyl group containing 6 to 12 carbon atoms and $R^8$ is hydrogen or an alkyl group containing 1 to 4 carbon atoms and (b) conjugated linoleic acid (CLA) and/or omega-3 and/or omega-6 fatty acids are subjected to enzymatic esterification or transesterification in the presence of glycerol.

9. Process according to embodiment 7 or 8, characterized in that the MCTs or the fatty acids on the one hand and the CLA and/or OF or their triglycerides on the other hand are used in a molar ratio of 1:1 to 20:1, based on the fatty acid equivalents.

10. Process according to any of embodiments 7 to 9, characterized in that the transesterification or esterification is carried out in the presence of vegetable or marine or microbial oils or mixtures thereof.

11. Process according to embodiment 10, characterized in that oils selected from the group consisting of rapeseed oil, soybean oil, sunflower oil, thistle oil, olive oil, tuna oil, sardine oil, salmon oil, mackerel oil and algal oils and other microbial oils rich in polyunsaturated fatty acids are used.

12. Process according to embodiment 10 or 11, characterized in that the MCTs or the fatty acids on the one hand and the oils on the other hand are used in a molar ratio of 5:1 to 1:5, based on fatty acid equivalents.

13. Process according to any of embodiments 7 to 12, characterized in that the enzymatic transesterification or esterification is carried out in the presence of at least one lipase or esterase.

14. Process according to any of embodiments 7 to 13, characterized in that lipases selected from the group of microbial lipases are used.

15. Process according to any of embodiments 7 to 14, characterized in that microbial lipases selected from the group consisting of *Rhizomucor*, *Rhizopus*, *Thermomyces*, *Pseudomonas* and *Candida* are used.

16. Process according to any of embodiments 7 to 15, characterized in that immobilized lipases are used.

17. Process according to any of embodiments 7 to 16, characterized in that the enzymatic esterification or transesterification is carried out at temperatures of 20 to 70° C.

18. Process according to any of embodiments 7 to 17, characterized in that the enzymatic esterification or transesterification is carried out over a period of 2 to 50 hours.

19. Process according to any of embodiments 7 to 18, characterized in that unreacted fatty acids, esters and monoglycerides are removed from the reaction products by distillation.

20. Process according to any of embodiments 7 to 19, characterized in that the reaction products are subsequently subjected to deodorization and/or bleaching.

21. Process according to any of embodiments 7 to 21, characterized in that antioxidants approved for use in foods are added to the mixture during and/or after the reaction.

22. Use of the mixture according to embodiment 1 as a food, food supplement, pharmaceutical preparation or animal feed.

23. Use according to embodiment 22, characterized in that the foods are edible oils or dietetic oils, grilling or frying oils and the like.

24. Use according to embodiment 22, characterized in that the mixture is a constituent of dressings, mayonnaises, margarine, dairy products, juices, confectionery and candies and the like.

25. Use according to embodiment 22, characterized in that the mixture is used for transesterification with hydrogenated fats and for producing lipids with adjustable solid fat contents, melting and crystallization behavior.

26. Use according to embodiment 22, characterized in that the mixture is used for parenteral nutrition.

27. Use according to any of embodiments 22 to 26, characterized in that the mixture is used in the form of emulsions containing phospholipids or capsules.

28. Use according to any of embodiments 22 to 27, characterized in that the lipid mixtures are used as a source of conjugated linoleic acid and/or omega-3 or omega-6 fatty acids and to reduce fatty tissue.

29. Use according to any of embodiments 22 to 28, characterized in that the lipid mixtures are used as dietetically active oils.

30. Use according to any of embodiments 22 to 29, characterized in that the lipid mixtures are used as an instant energy source and for building up muscle mass in sports nutrition.

31. Use of the mixture according to embodiment 1 for the production of a medicament for treating disorders of the metabolism.

EXAMPLES

The practice of the invention is further illustrated by the following examples which are not intended to limit the scope of the invention.

Example 1

Production of Structured Lipids by Enzymatic Transesterification

In four batches, quantities of 25 g MCT (medium-chain triglyceride, Myritol® 318, Cognis Deutschland GmbH & Co. KG), 5 g CLA triglyceride (Tonalin® TG 80, Cognis Deutschland GmbH & Co. KG) and 20 g rapeseed oil were weighed into a flask. Quantities of 2.5 g immobilized *Rhizomucor miehei* lipase were added to batches 1 and 3 while quantities of 2.5 g immobilized *Thermomyces lanugenosus* lipase were added to batches 2 and 4. Batches 1 and 2 were incubated while shaking at 45° C. while batches 3 and 4 were incubated while shaking at 40° C. After 5 h and 29 h (batches 1 and 2 only), samples were taken and analyzed by gas chromatography. The results are set out in Table 1 and comprise the composition in % area (GC) and the acid value.

TABLE 1

Composition of the reaction product

| | Composition | | | | | |
|---|---|---|---|---|---|---|
| | 1a | 1b | 1c | 1d | 1e | 1f |
| Batch No. | 1 | 1 | 2 | 2 | 3 | 4 |
| Reaction time [h] | 5 | 29 | 5 | 29 | 5 | 5 |
| Glyceride distribution [% area] | | | | | | |
| FA (medium-chain) | 2.6 | 2.6 | 2.4 | 2.3 | 2.7 | 2.4 |
| FA (long-chain) | 1.7 | 2.1 | 2.0 | 2.0 | 2.0 | 2.0 |
| MG (medium-chain) | 0 | 0 | 0 | 0 | 0 | 0 |
| MG (long-chain) | 0 | 0 | 0 | 0 | 0 | 0 |
| DG (2x medium-chain) | 4.2 | 3.6 | 3.4 | 3.2 | 4.0 | 3.4 |
| DG (1x medium-chain, 1x long-chain) | 2.0 | 1.9 | 1.5 | 1.4 | 2.0 | 1.7 |
| DG (2x long-chain) | 0.4 | 0.5 | 0.5 | 0.6 | 0.9 | 0.3 |
| TG (3x medium-chain) | 34.4 | 23.9 | 24.7 | 21.4 | 29.7 | 21.6 |
| TG (2x medium, 1x long-chain) | 23.1 | 35.1 | 37.8 | 39.3 | 28.6 | 39.3 |
| TG (1x medium, 2x long-chain) | 15.3 | 24.3 | 23.0 | 26.1 | 21.1 | 25.3 |
| TG (3x long-chain) | 16.3 | 6.0 | 4.7 | 3.7 | 9.2 | 4.1 |
| Acid value | 7 | 7 | 7 | 8 | 8 | 7 |

The Examples show that the transesterification with both immobilized lipases proceeds with excellent yields both at 45° C. and at 60° C.

Example 2

Production of Structured Lipids by Enzymatic Transesterification; Product Purification by Distillation 750 g MCT (Myritol® 318), 150 g CLA triglyceride (Tonalin® TG 80) and 600 g rapeseed oil were weighed into a flask. The mixture was blanketed with nitrogen and, after the addition of 75 g immobilized *Thermomyces lanugenosus* lipase, was incubated while shaking for 24 h. After 5 h and 24 h, samples were taken and analyzed for their acid values by gas chromatography. After 24 h, the enzyme was removed from the crude product by filtration. The crude product was purified by short-path distillation at 200° C. under a vacuum of 0.4 mbar. The bottom product and the distillate were then analyzed by gas chromatography and wet chemical analysis. The distribution of the glycerides and the fatty acid spectrum were analyzed and the oleochemical data of the bottom product were determined. The bottom product was refined for 15 mins. at 80° C. with 50% by weight sodium hydroxide (2× molar quantity, based on free fatty acids), treated for 15 mins. at 100° C. with 2% bleaching clay (Tonsil) and then washed with 5% by weight water. The water phase was then removed and the residue dried in vacuo. 500 ppm mixed tocopherols (Covi-ox T-90) were added to the end product for stabilization. The results are set out in Table 2 and comprise the composition in % area (GC) and the acid value. The Lovibond and Gardner color values before and after refining and bleaching are set out in Table 3.

TABLE 2

Composition of the reaction product

| | Composition | | | |
|---|---|---|---|---|
| Product | 2a 5 h Synthesis | 2b 24 h Synthesis | 2c Distillation Bottom prod. | 2d Distillation Distillate |
| Glyceride distribution [% area] | | | | |
| FA (medium-chain) | 1.5 | 1.3 | 0.1 | 31.6 |
| FA (long-chain) | 0.7 | 0.8 | 0.7 | 16.6 |
| MG (medium-chain) | 0 | 0 | 0 | 0.8 |
| MG (long-chain) | 0 | 0 | 0 | 0 |
| DG (2x medium-chain) | 2.3 | 2.0 | 1.4 | 16.8 |
| DG (1x medium, 1x long-chain) | 0.5 | 1.0 | 0.7 | 0.4 |
| DG (2x long-chain) | 0.3 | 0.5 | 0.4 | 0 |
| TG (3x medium-chain) | 33.7 | 21.6 | 21.6 | 31.5 |
| TG (2x medium-, 1x long-chain) | 30.2 | 40.9 | 41.7 | 2.2 |
| TG (1x medium, 2x long-chain) | 16.0 | 27.5 | 28.7 | 0.1 |
| TG (3x long-chain) | 14.8 | 4.4 | 4.7 | 0 |
| Fatty acid spectrum | | | | |
| C8 | | 30.0 | 29.7 | 49.9 |
| C10 | | 13.5 | 13.9 | 19.0 |
| C16:0 | | 2.4 | 2.4 | 2.2 |
| C18:0 | | 1.2 | 1.2 | 0.8 |
| C18:1 | | 29.8 | 39.9 | 17.4 |
| C18:2 | | 9.5 | 9.4 | 4.3 |
| C18:3 | | 4.0 | 3.9 | 1.7 |
| C9, t11 CLA | | 4.9 | 4.8 | 2.4 |
| t10, c12 CLA | | 4.7 | 4.7 | 2.2 |
| Wet chemical data | | | | |
| Acid value | 5 | 5 | 1.3 | 137 |
| Hydroxyl value | | | 6.4 | |
| Iodine value | | | 57 | |
| Saponification value | | | 261 | |
| Peroxide value | | | 5.0 | |

TABLE 3

Description of the reaction product

| Color values | Bottom product after distillation | Product bleached, refined | Rapeseed oil |
|---|---|---|---|
| Gardner | 3.4 | 1.0 | 1.8 |
| Lovibond 5¼ | Ly 24.0; Lr 2.8 | Ly 7.8; Lr 1.0 | Ly 12.0; Lr 1.4 |
| Acid value | 1.3 | 0.5 | 0.4 |

The Examples show that high-quality structured lipids can be produced by enzymatic transesterification and purification by distillation.

Example 3

Production of Structured Lipids by Enzymatic Transesterification; Product Purification by Distillation 450 g MCT (Myritol® 318), 150 g CLA triglyceride (Tonalin® TG 80) and 900 g rapeseed oil were weighed into a flask. The mixture was blanketed with nitrogen and, after the addition of 75 g immobilized *Thermomyces lanugenosus* lipase, was incubated while shaking for 24 h. After 5 h and 24 h, samples were taken and analyzed for their acid values by gas chromatography. After 24 h, the enzyme was removed from the crude product by filtration. The crude product was purified by short-path distillation at 200° C. under a vacuum of 0.4 mbar. The bottom product and the distillate were then analyzed by gas chromatography and wet chemical analysis. The distribution of the glycerides and the fatty acid spectrum were analyzed and the oleochemical data of the bottom product were determined. The bottom product was refined for 15 mins. at 80° C. with 50% by weight sodium hydroxide (2× molar quantity, based on free fatty acids), treated for 15 mins. at 100° C. with 2% by weight bleaching clay (Tonsil) and finally washed with 5% by weight water. The water phase was then removed and the product dried in vacuo. 500 ppm mixed tocopherols (Covi-ox T-90) were added to the end product for stabilization. The results are set out in Table 4 and comprise the composition in % area (GC) and the acid value. The Lovibond and Gardner color values before and after refining and bleaching are set out in Table 5.

TABLE 4

Composition of the reaction product

| Product | Composition | | | |
|---|---|---|---|---|
| | 3a 5 h Synthesis | 3b 24 h Synthesis | 3c Distillation Bottom prod. | 3d Distillation Distillate |
| Glyceride distribution [% area] | | | | |
| FA (medium-chain) | 1.0 | 0.9 | 0 | 29.2 |
| FA (long-chain) | 0.8 | 1.1 | 0.7 | 35.1 |
| MG (medium-chain) | 0 | 0 | 0 | 0.9 |
| MG (long-chain) | 0 | 0 | 0 | 0 |
| DG (2x medium-chain) | 0.9 | 0.7 | 0.7 | 13.4 |
| DG (1x medium-, 1x long-chain) | 0.5 | 0.9 | 0.5 | 0.9 |
| DG (2x long-chain) | 0.5 | 1.0 | 0.5 | 0 |
| TG (3x medium-chain) | 16.8 | 8.5 | 9.5 | 18.3 |
| TG (2x medium-, 1x long-chain) | 25.3 | 30.8 | 32.5 | 2.1 |
| TG (1x medium, 2x long-chain) | 26.3 | 41.3 | 43.2 | 0.1 |
| TG (3x long-chain) | 27.9 | 14.8 | 12.4 | 0 |
| Fatty acid spectrum | | | | |
| C8 | | 19.9 | 20.5 | 35.0 |
| C10 | | 8.8 | 9.2 | 14.2 |
| C16:0 | | 3.0 | 3.0 | 3.7 |
| C18:0 | | 1.4 | 1.3 | 1.2 |
| C18:1 | | 39.3 | 38.5 | 29.4 |
| C18:2 | | 12.7 | 12.6 | 7.5 |
| C18:3 | | 5.5 | 5.5 | 3.2 |
| C9, t11 CLA | | 4.8 | 4.7 | 3.0 |
| t10, c12 CLA | | 4.7 | 4.6 | 2.9 |
| Wet chemical data | | | | |
| Acid value | 5 | 5 | 1.4 | 168 |
| Hydroxyl value | | | 6.2 | |
| Iodine value | | | 66 | |
| Saponification value | | | 239 | |
| Peroxide value | | | 9.4 | |

TABLE 5

Description of the reaction product

| Color values | Bottom product after distillation | Product bleached, refined | Rapeseed oil |
|---|---|---|---|
| Gardner | 3.6 | 1.1 | 1.8 |
| Lovibond 5¼ | Ly 26.0; Lr 3.1 | Ly 8.2; Lr 0.9 | Ly 12.0; Lr 1.4 |
| Acid value | 1.4 | 0.4 | 0.4 |

The Examples show that high-quality structured lipids can be produced by enzymatic transesterification and purification by distillation.

Example 4

Production of Structured Lipids by Enzymatic Synthesis

In two batches, quantities of 30 g caprylic acid, 12 g capric acid, 9 g 80% by weight CLA fatty acid (Tonalin® CLA 80; Cognis Deutschland GmbH & Co. KG), 9 g glycerol and 40 g rapeseed oil were weighed into a flask. 5 g immobilized *Candida antarctica B* lipase were added to batch 1 while 5 g immobilized *Rhizomucor miehei* lipase were added to batch 2. The batches were incubated with stirring under nitrogen at 60° C. under a vacuum of 20 mbar. Samples were taken after 6 h and 24 h and analyzed by gas chromatography. The results are set out in Table 6 and comprise the composition in % area (GC) and the acid value (as measured after 50 h).

TABLE 6

Composition of the reaction product

| | Composition | | | |
|---|---|---|---|---|
| | 4a | 4b | 4c | 4d |
| Batch No. | 1 | 1 | 2 | 2 |
| Reaction time [h] | 6 | 24 | 6 | 24 |
| Glyceride distribution [% area] | | | | |
| FA (medium-chain) | 11.3 | 5.9 | 16.9 | 10.4 |
| FA (long-chain) | 7.2 | 5.1 | 10.3 | 7.8 |
| MG (medium-chain) | 0 | 0 | 0 | 0 |
| MG (long-chain) | 0 | 0 | 0 | 0 |
| DG (2x medium-chain) | 6.9 | 0.5 | 12.8 | 8.1 |
| DG (1x medium. 1x long-chain) | 6.7 | 0 | 21.1 | 2.5 |
| DG (2x long-chain) | 1.3 | 0.7 | 1.4 | 0.9 |
| TG (3x medium-chain) | 20.3 | 21.6 | 3.2 | 16.5 |
| TG (2x medium-, 1x long-chain) | 20.4 | 34.8 | 13.6 | 27.8 |
| TG (1x medium, 2x long-chain) | 11.7 | 22.9 | 15.2 | 21.9 |
| TG (3x long-chain) | 14.2 | 8.4 | 5.0 | 4.1 |
| Acid value | 21 | | 20 | |

The Examples show that synthesis and simultaneous transesterification are possible both with immobilized *Candida B* lipase and with immobilized *Rhizomucor miehei* lipase. The *Candida B* lipase shows better synthesis activity while the *Rhizomucor miehei* lipase has better transesterification activity.

Example 5

Production of Structured Lipids by Enzymatic Synthesis; Product Purification by Distillation 450 g caprylic acid, 180 g capric acid, 135 g 80% by weight CLA fatty acid (Tonalin® CLA 80), 142.5 g glycerol and 900 g rapeseed oil were weighed into a heatable double-jacketed reactor. 37.5 g immobilized *Candida antarctica B* lipase and 37.5 g immobilized *Rhizomucor miehei* lipase were added to the batch which was then incubated with stirring under nitrogen for 48 h at 60° C. in a vacuum of 20 mbar. After 5 h, 24 h and 48 h, samples were taken and analyzed for their acid values by gas chromatography. After 48 h, the enzyme was removed from the crude product by filtration. The crude product was then purified by short-path distillation at 200° C. under a vacuum of 0.4 mbar. The bottom product and the distillate were then analyzed by gas chromatography and wet chemical analysis. The distribution of the glycerides and the fatty acid spectrum were analyzed and the oleochemical data of the bottom product were determined. The bottom product was refined for 15 mins. at 80° C. with 50% by weight sodium hydroxide (2× molar quantity, based on free fatty acids), treated for 15 mins. at 100° C. with 2% bleaching clay (Tonsil) and finally washed with 5% by weight water. The water phase was then removed and the residue dried in vacuo. 500 ppm mixed tocopherols (Covi-ox T-90) were added to the end product for stabilization. The results are set out in Table 7 and comprise the composition in % area (GC) and the acid value. The acid values and the Lovibond and Gardner color values before and after refining and bleaching are set out in Table 8.

TABLE 7

Composition of the reaction product

| Product | 5a<br>5 h<br>Synthesis | 5b<br>24 h<br>Synthesis | 5c<br>48 h<br>Synthesis | 5d<br>Distillation<br>Bottom prod. | 5e<br>Distillation<br>Distillate |
|---|---|---|---|---|---|
| Glyceride distribution [% area] | | | | | |
| FA (medium-chain) | 16.4 | 4.0 | 3.8 | 0 | 18.8 |
| FA (long-chain) | 8.7 | 4.1 | 3.1 | 0.2 | 22.7 |
| MG (medium-chain) | 0 | 0 | 0 | 0 | 0.3 |
| MG (long-chain) | 0 | 0 | 0 | 0 | 0 |
| DG (2× medium-chain) | 13.6 | 0.5 | 0.2 | 0 | 3.7 |
| DG (1× medium, 1× long-chain) | 9.9 | 0.8 | 0 | 0.2 | 0.3 |
| DG (2× long-chain) | 0.9 | 0.4 | 0.6 | 0.6 | 0 |
| TG (3× medium-chain) | 10.1 | 17.4 | 18.3 | 12.9 | 49.6 |
| TG (2× medium-, 1× long-chain) | 12.6 | 39.3 | 39.9 | 45.9 | 4.5 |
| TG (1× medium, 2× long-chain) | 10.8 | 28.3 | 29.3 | 34.7 | 0.1 |
| TG (3× long-chain) | 16.5 | 5.2 | 4.8 | 5.5 | 0 |
| Fatty acid spectrum | | | | | |
| C8 | | | 30.9 | 27.2 | 56.0 |
| C10 | | | 13.9 | 13.8 | 16.9 |
| C16:0 | | | 2.5 | 2.5 | 1.4 |
| C18:0 | | | 1.2 | 1.2 | 0.6 |
| C18:1 | | | 29.4 | 31.7 | 15.1 |
| C18:2 | | | 9.5 | 10.3 | 3.8 |
| C18:3 | | | 3.9 | 4.3 | 1.6 |
| C9, t11 CLA | | | 4.3 | 4.6 | 2.4 |
| t10, c12 CLA | | | 4.3 | 4.5 | 2.1 |
| Wet chemical data | | | | | |
| Acid value | | 19 | 13 | 0.4 | 99 |
| Hydroxyl value | | | | 2.5 | |
| Iodine value | | | | 57 | |
| Saponification value | | | | 251 | |
| Peroxide value | | | | 4.0 | |

TABLE 8

Description of the reaction product

| Color values | Bottom product after distillation | Product bleached, refined | Rapeseed oil |
|---|---|---|---|
| Gardner | 3.5 | 0.8 | 1.8 |
| Lovibond 5¼ | Ly 22.0; Lr 3.0 | Ly 6.4; Lr 0.9 | Ly 12.0; Lr 1.4 |
| Acid value | 0.4 | 0.1 | 0.4 |

The Examples show that high-quality structured lipids can be produced by enzymatic transesterification and purification by distillation.

Example 6

Production of Structured Lipids by Coupled Enzymatic Synthesis and Transesterification; Product Purification by Distillation 450 g caprylic acid, 180 g capric acid, 135 g 80% by weight CLA fatty acid (Tonalin® CLA 80), 142.5 g glycerol and 900 g rapeseed oil were weighed into a heatable double-jacketed reactor. 50 g immobilized *Candida antarctica B* lipase were added to the batch which was then incubated with stirring under nitrogen for 24 h at 60° C. in a vacuum of 5 mbar. After 5 h and 24 h, samples were taken and analyzed for their acid values by gas chromatography. After 24 h, the enzyme was removed from the crude product by filtration and, for further transesterification, was pumped through a column packed with immobilized *Thermomyces lanugenosus*. To this end, the column was packed with immobilized lipase and was operated at room temperature with a flow rate of 50 g/h. The transesterified product was analyzed for its acid value by gas chromatography and was then purified by short-path distillation at 200° C. under a vacuum of 0.4 mbar. The bottom product and the distillate were then analyzed by gas chromatography and wet chemical analysis. The distribution of the glycerides and the fatty acid spectrum were analyzed and the oleochemical data of the bottom product were determined. The bottom product was then refined for 15 mins. at 80° C. with 50% by weight sodium hydroxide (2× molar quantity, based on free fatty acids), treated for 15 mins. at 100° C. with 2% by weight bleaching clay (Tonsil) and washed with 5% by weight water. The water phase was then removed and the product dried in vacuo. 500 ppm mixed tocopherols (Covi-ox T-90) were added to the end product for stabilization. The results are set out in Table 9 and comprise the composition in % area (GC) and the acid value. The acid values and the color values before and after refining and bleaching are set out in Table 10.

immobilized *Rhizomucor miehei* lipase were added to batches 1 and 2 while 2.5 g immobilized *Thermomyces lanugenosus* lipase were added to batch 3. Batches 1 and 3 were incubated while shaking at 45° C. while batch 3 was incubated while shaking at 60° C. After 5 h, 24 h and 48 h (after 5 h only for batch 3), samples were taken and analyzed by gas chromatography. The results are set out in Table 11 and comprise the composition in % area (GC) and the acid value.

TABLE 9

Composition of the reaction product

| Product | 6a 5 h Synthesis | 6b 24 h Synthesis | 6c 48 h Synthesis | 6d Distillation Bottom prod. | 6e Distillation Distillate |
|---|---|---|---|---|---|
| Glyceride distribution [% area] | | | | | |
| FA (medium-chain) | 14.8 | 4.2 | 3.5 | 0 | 20.5 |
| FA (long-chain) | 5.6 | 3.4 | 3.0 | 0.3 | 24.4 |
| MG (medium-chain) | 0 | 0 | 0 | 0 | 0.3 |
| MG (long-chain) | 0 | 0 | 0 | 0 | 0 |
| DG (2x medium-chain) | 15.1 | 1.7 | 1.8 | 0.2 | 12.4 |
| DG (1x medium, 1x long-chain) | 5.3 | 0.4 | 1.0 | 0.5 | 1.0 |
| DG (2x long-chain) | 0.8 | 0.9 | 0.7 | 0.8 | 0 |
| TG (3x medium-chain) | 16.9 | 21.0 | 18.7 | 16.0 | 38.4 |
| TG (2x medium-, 1x long-chain) | 7.9 | 34.8 | 37.9 | 42.9 | 3.0 |
| TG (1x medium, 2x long-chain) | 4.0 | 25.1 | 27.4 | 32.2 | 0 |
| TG (3x long-chain) | 29.6 | 8.5 | 6.0 | 7.1 | 0 |
| Fatty acid spectrum | | | | | |
| C8 | | | 28.2 | 27.5 | 50.1 |
| C10 | | | 13.4 | 13.8 | 16.5 |
| C16:0 | | | 2.4 | 2.5 | 1.8 |
| C18:0 | | | 1.2 | 1.2 | 0.8 |
| C18:1 | | | 31.2 | 31.6 | 18.5 |
| C18:2 | | | 10.0 | 10.3 | 4.6 |
| C18:3 | | | 4.2 | 4.1 | 1.9 |
| C9, t11 CLA | | | 4.8 | 4.5 | 3.1 |
| t10, c12 CLA | | | 4.6 | 4.5 | 2.7 |
| Wet chemical data | | | | | |
| Acid value | 50 | 20 | 16 | 0.4 | 115 |
| Hydroxyl value | | | | 5.4 | |
| Iodine value | | | | 68 | |
| Saponification value | | | | 255 | |
| Peroxide value | | | | 5.2 | |

TABLE 10

Description of the reaction product

| Color values | Bottom product after distillation | Product bleached, refined | Rapeseed oil |
|---|---|---|---|
| Gardner | 3.9 | 0.8 | 1.8 |
| Lovibond 5¼ | Ly 27.0; Lr 3.7 | Ly 6.3; Lr 0.8 | Ly 12.0; Lr 1.4 |
| Acid value | 0.4 | 0.4 | 0.4 |

The Examples show that high-quality structured lipids can be produced by enzymatic synthesis and transesterification after purification by distillation.

Example 7

Production of Structured Lipids by Enzymatic Transesterification

In three batches, quantities of 17.5 g caprylic acid, 7.5 g capric acid, 5 g CLA triglyceride (Tonalin® TG 80) and 20 g rapeseed oil were weighed into a flask. Quantities of 2.5 g

TABLE 11

Composition of the reaction product

| | Composition | | | | | | |
|---|---|---|---|---|---|---|---|
| | 7a | 7b | 7c | 7d | 7e | 7f | 7g |
| Batch No. | 1 | 1 | 1 | 2 | 3 | 3 | 3 |
| Reaction time [h] | 5 h | 24 h | 48 h | 5 h | 5 h | 24 h | 48 h |
| Glyceride distribution [% area] | | | | | | | |
| FA (medium-chain) | 52.2 | 49.0 | 40.7 | 50.8 | 57.1 | 55.8 | 51.7 |
| FA (long-chain) | 8.2 | 20.9 | 24.3 | 11.3 | 3.7 | 9.1 | 12.6 |
| MG (medium-chain) | 0 | 0 | 0 | 0 | 0 | 0 | 0 |
| MG (long-chain) | 0 | 0 | 0 | 0 | 0 | 0 | 0 |
| DG (2x medium-chain) | 0.7 | 0.5 | 1.6 | 0.7 | 0.2 | 0 | 0.4 |
| DG (1x medium, 1x long-chain) | 1.2 | 0.7 | 1.8 | 1.0 | 0.5 | 0.5 | 1.4 |
| DG (2x long-chain) | 0.2 | 0 | 0.2 | 0.2 | 0.9 | 1.9 | 1.4 |
| TG (3x medium-chain) | 0 | 0 | 0.6 | 0 | 0 | 0 | 0.2 |
| TG (2x medium, 1x long-chain) | 2.0 | 6.1 | 10.1 | 3.3 | 2.3 | 1.0 | 3.6 |

TABLE 11-continued

Composition of the reaction product

| | \multicolumn{7}{c|}{Composition} |
| --- | --- | --- | --- | --- | --- | --- | --- |
| | 7a | 7b | 7c | 7d | 7e | 7f | 7g |
| TG (1x medium, 2x long-chain) | 7.9 | 15.3 | 16.5 | 11.4 | 3.5 | 8.2 | 12.6 |
| TG (3x long-chain) | 27.6 | 7.5 | 4.2 | 21.1 | 31.8 | 23.5 | 16.1 |
| Acid value | 182 | 184 | 184 | 188 | 188 | 190 | 190 |

The Examples show that the transesterification can be successfully carried out with both immobilized lipases both at 45° C. and at 60° C. In the presence of high concentrations of free acid, *Rhizomucor miehei* lipase shows a comparatively faster reaction.

Example 8

Production of Structured Lipids by Enzymatic Transesterification; Product Purification by Distillation 875 g caprylic acid, 375 g capric acid, 250 g CLA triglyceride (Tonalin® TG 80) and 1,000 g rapeseed oil were weighed into a flask. The mixture was blanketed with nitrogen and, after the addition of 150 g immobilized *Rhizomucor miehei* lipase, was incubated while shaking for 48 h. For the first 24 h, incubation was carried out at 45° C., after which the temperature was increased to 60° C. After 5 h, 24 h and 48 h, samples were taken and analyzed for their acid values by gas chromatography. After 48 h, the enzyme was removed from the crude product by filtration. The crude product was purified by short-path distillation twice at 200° C. in a vacuum of 0.4 mbar. The bottom product obtained and the purified distillate were then analyzed by gas chromatography and wet chemical analysis. The distribution of the glycerides and the fatty acid spectrum were analyzed and the oleochemical data of the bottom product were determined. The bottom product was refined for 15 mins. at 80° C. with 50% by weight sodium hydroxide (2× molar quantity, based on free fatty acids), treated for 15 mins. at 100° C. with 2% bleaching clay (Tonsil) and then washed with 5% by weight water. The water phase was then removed and the residue dried in vacuo. 500 ppm mixed tocopherols (Covi-ox T-90) were added to the end product for stabilization. The acid values and the Lovibond and Gardner color values before and after refining were determined. The results are set out in Table 12 and comprise the composition in % area (GC) and the acid value. The acid values and Lovibond and Gardner color values before and after refining and bleaching are set out in Table 13.

TABLE 13

Composition of the reaction product

| | \multicolumn{5}{c|}{Composition} |
| --- | --- | --- | --- | --- | --- |
| Product | 8a<br>5 h<br>Synthesis | 8b<br>24 h<br>Synthesis | 8c<br>48 h<br>Synthesis | 8d<br>Distillation<br>Bottom prod. | 8e<br>Distillation<br>Distillate |
| \multicolumn{6}{c}{Glyceride distribution [% area]} |
| FA (medium-chain) | 54.0 | 48.0 | 44.0 | 0.1 | 59.2 |
| FA (long-chain) | 7.1 | 18.5 | 26.0 | 1.3 | 37.8 |
| MG (medium-chain) | 0 | 0 | 0 | 0 | 0.1 |
| MG (long-chain) | 0 | 0 | 0 | 0 | 0.1 |
| DG (2x medium-chain) | 0.4 | 0.9 | 0.4 | 0.1 | 0.7 |
| DG (1x medium, 1x long-chain) | 0.3 | 0.3 | 0.7 | 0.8 | 0 |
| DG (2x long-chain) | 0.5 | 0.3 | 0.5 | 0.6 | 0 |
| TG (3x medium-chain) | 0 | 0.5 | 1.3 | 5.6 | 1.1 |
| TG (2x medium, 1x long-chain) | 0.9 | 6.2 | 8.7 | 30.4 | 0.1 |
| TG (1x medium, 2x long-chain) | 8.1 | 17.6 | 15.7 | 48.3 | 0 |
| TG (3x long-chain) | 28.7 | 7.7 | 2.7 | 12.8 | 0 |
| \multicolumn{6}{c}{Fatty acid spectrum} |
| C8 | | | | 35.3 | 16.9 | 41.9 |
| C10 | | | | 17.1 | 8.4 | 19.3 |
| C16:0 | | | | 2.2 | 2.4 | 2.0 |
| C18:0 | | | | 1.1 | 1.3 | 0.9 |
| C18:1 | | | | 25.4 | 38.6 | 21.7 |
| C18:2 | | | | 7.2 | 15.0 | 5.3 |
| C18:3 | | | | 3.2 | 6.3 | 2.1 |
| C9, t11 CLA | | | | 4.3 | 5.5 | 3.5 |
| t10, c12 CLA | | | | 4.1 | 5.6 | 3.3 |
| \multicolumn{6}{c}{Wet chemical data} |
| Acid value | | | 185 | 3.1 | 290 |
| Hydroxyl value | | | | 6.6 | |
| Iodine value | | | | 62 | |
| Saponification value | | | | 234 | |
| Peroxide value | | | | 4.1 | |

TABLE 13

Description of the reaction product

| Color values | Bottom product after distillation | Product bleached, refined | Rapeseed oil |
|---|---|---|---|
| Gardner | 7.1 | 3.1 | 1.8 |
| Lovibond 5¼ | Ly 107; Lr 15.2 | Ly 34.0; Lr 3.9 | Ly 12.0; Lr 1.4 |
| Acid value | 3.1 | 0.6 | 0.4 |

The Examples show that high-quality structured lipids can be produced by enzymatic transesterification and purification by distillation.

Example 9

Production of Structured Lipids with Various Vegetable and Animal Oils

Quantities of 7.5 g MCT Myritol® 318, 1.5 g CLA triglyceride (Tonalin® TG 80), 0.5 g Lipozym® TL IM (*Thermmyces lanugenosus*) and the following vegetable and animal oils were introduced into five sealable flasks:

Batch 1: 1.5 g tuna oil and 4.5 g rapeseed oil

Batch 2: 1.5 g mackerel oil and 4.5 g rapeseed oil

Batch 3: 1.5 g linseed oil and 4.5 g soybean oil

Batch 4: 1.5 g linseed oil and 4.5 g sunflower oil

Batch 5: 3.0 g olive oil and 3.0 g rapeseed oil

The flasks were sealed and incubated while shaking for 24 h at 45° C. On completion of the reaction, a sample was silylated and analyzed by gas chromatography for the distribution of glycerides, the triglyceride content being standardized to 100. In addition, a sample was methylated and the fatty acid composition was determined by gas chromatography. The results are set out in Table 14 as the composition in % area (GC).

TABLE 14

Composition of the reaction product

| | Composition | | | | |
|---|---|---|---|---|---|
| | 9a | 9b | 9c | 9d | 9e |
| Glyceride distribution [% area] | | | | | |
| 3x medium-chain | 35.3 | 36.4 | 33.6 | 32.5 | 32.1 |
| 2x medium, 1x long-chain | 34.3 | 33.0 | 34.6 | 34.8 | 33.3 |
| 1x medium, 2x long-chain | 18.7 | 18.0 | 18.4 | 20.5 | 20.4 |
| 3x long-chain | 11.7 | 12.7 | 13.4 | 12.1 | 14.3 |
| Fatty acid spectrum | | | | | |
| C8 | 38.2 | 37.4 | 37.0 | 36.5 | 36.5 |
| C10 | 16.6 | 16.3 | 16.0 | 15.8 | 16.0 |
| C16:0 | 3.4 | 3.3 | 4.2 | 2.6 | 2.8 |
| C18:0 | 1.3 | 1.3 | 1.8 | 1.7 | 1.4 |
| C18:1 | 20.6 | 20.8 | 10.5 | 12.3 | 28.7 |
| C18:2 | 6.2 | 6.5 | 17.2 | 18.6 | 5.8 |
| C18:3 | 2.2 | 2.3 | 6.0 | 4.7 | 1.6 |
| C9, t11 CLA | 4.0 | 4.3 | 3.6 | 3.9 | 3.6 |
| t10, c12 CLA | 3.8 | 4.1 | 3.6 | 3.9 | 3.5 |
| C20:5 | 2.2 | 2.3 | 0 | 0 | 0 |
| C22:6 | 1.5 | 1.4 | 0 | 0 | 0 |

The Examples show that the production of structured lipids can be successfully carried out irrespective of the nature of the fats and oils used.

Example 10

Production of Structured Lipids of the ABA Type with Various Vegetable and Animal Oils Examples 10a to 10e were repeated with the 7.5 g MCT being replaced by 7.5 g caprylic acid. The results are set out in Table 15 as the composition in % area (GC).

TABLE 15

Composition of the reaction product

| | Composition | | | | |
|---|---|---|---|---|---|
| | 10a | 10b | 10c | 10d | 10e |
| Glyceride distribution [% area] | | | | | |
| 3x medium-chain | 2.0 | 1.5 | 1.8 | 1.8 | 1.7 |
| 2x medium, 1x long-chain | 26.9 | 14.7 | 25.9 | 26.4 | 24.6 |
| 1x medium, 2x long-chain | 39.2 | 33.6 | 38.3 | 38.0 | 37.2 |
| 3x long-chain | 31.8 | 40.2 | 34.0 | 33.7 | 36.5 |

These Examples also show that the production of structured lipids can be successfully carried out irrespective of the nature of the fats and oils used.

Example 11

Production of Structured Lipids with Various Contents of Medium-Chain Fatty Acids MCT (Mytritol® 318), CLA triglyceride (Tonalin® TG 80) and rapeseed oil were weighed in various quantities into four sealable flasks. 5 g MCT, 1.5 g CLA triglyceride and 8.5 g rapeseed oil were used in batch 1, 7.5 g, 1.5 g and 6 g in the same order in batch 2, 10 g, 1.5 g and 3.5 g in batch 3 and 7.5 g, 3 g and 4.5 g in batch 4. After addition of 0.5 g Lipozym® TL IM, the flasks were sealed and incubated for 24 h at 45° C. On completion of the reaction, a sample was silylated and analyzed by gas chromatography for the distribution of glycerides. The content of triglyceride species was determined, the triglyceride content being standardized to 100. In addition, a sample was methylated and the fatty acid composition was determined by gas chromatography. The results are set out in Table 16 as the composition in % area (GC).

TABLE 16

Composition of the reaction product

| | Composition | | | |
|---|---|---|---|---|
| | 11a | 11b | 11c | 11d |
| Glyceride distribution [% area] | | | | |
| 3x medium-chain | 16.0 | 33.2 | 52.9 | 34.1 |
| 2x medium, 1x long-chain | 30.8 | 34.3 | 30.3 | 28.4 |
| 1x medium, 2x long-chain | 27.3 | 20.8 | 10.5 | 18.3 |
| 3x long-chain | 25.8 | 11.7 | 6.2 | 19.2 |
| Fatty acid spectrum | | | | |
| C8 | 23.6 | 36.2 | 49.5 | 35.2 |
| C10 | 10.3 | 15.9 | 21.5 | 15.3 |
| C16:0 | 3.1 | 2.1 | 1.2 | 1.7 |
| C18:0 | 1.4 | 1.1 | 0.7 | 1.2 |

TABLE 16-continued

Composition of the reaction product

| | Composition | | | |
|---|---|---|---|---|
| | 11a | 11b | 11c | 11d |
| C18:1 | 36.7 | 25.6 | 14.0 | 21.3 |
| C18:2 | 12.1 | 8.2 | 4.3 | 6.5 |
| C18:3 | 4.8 | 3.1 | 1.6 | 2.6 |
| C9, t11 CLA | 4.0 | 4.0 | 3.6 | 8.2 |
| t10, c12 CLA | 4.0 | 3.9 | 3.5 | 8.0 |

The Examples show that the production of structured lipids can be successfully carried out irrespective of ratios used.

Example 12

Production of Structured Lipids of the ABA Type with Various Contents of Medium-Chain Fatty Acids Examples 11 a to 11 d were repeated with the MCT replaced by the same quantity by weight of caprylic acid. On completion of the reaction, a sample was silylated and analyzed by gas chromatography for the distribution of glycerides. The content of triglyceride species was determined, the triglyceride content being standardized to 100. In addition, a sample was methylated and the fatty acid composition was determined by gas chromatography. The results are set out in Table 17 as the composition in % area (GC).

TABLE 17

Composition of the reaction product

| | Composition | | | |
|---|---|---|---|---|
| | 12a | 12b | 12c | 12d |
| Glyceride distribution [% area] | | | | |
| 3x medium-chain | 1.5 | 1.3 | 0.7 | 2.1 |
| 2x medium, 1x long-chain | 31.3 | 23.6 | 16.2 | 27.4 |
| 1x medium, 2x long-chain | 51.2 | 35.0 | 18.8 | 37.9 |
| 3x long-chain | 16.0 | 40.1 | 64.3 | 32.6 |

These Examples also show that the production of structured lipids can be successfully carried out irrespective of ratios used.

Example 13

Comparison of the Regioselective Fatty Acid Composition of the Structured Lipids The distilled lipids from Example 2, 3, 5, 6 and 8 were analyzed for their regioselective fatty acid structure. To this end, a regioselective enzymatic alcoholysis was carried out with immobilized *Thermomyces lanugenosus* at 20° C. Quantities of 0.5 g structured lipid were mixed with 1.5 g ethanol and incubated while stirring with lipase. The regioselectively split products were silylated and analyzed by gas chromatography. The peak areas of the ethyl esters formed were evaluated and the total sum of the ethyl esters was equated with 100. To determine the fatty acid composition in the 2 position, the difference between the total fatty acid distribution and the distribution in the 1 and 3 positions was calculated. The total distribution was determined through methylation of the structured lipids and gas chromatographic analysis. To determine the distribution in the 2 position, the difference in weight between the methyl esters and the analyzed ethyl esters was extrapolated by computer. The total fatty acids in the 1,3 and 2 positions was always standardized to 100. The results are set out in Table 18 as % area (GC).

TABLE 18

Composition of the reaction product

| Fatty acid | Total | 1, 3 Position | 2 Position |
|---|---|---|---|
| Sample from Example 2 | | | |
| C8 | 29.7 | 31.7 | 25.7 |
| C10 | 13.9 | 13.8 | 14.0 |
| C16:0 | 2.4 | 2.5 | 2.2 |
| C18:0 | 1.2 | 1.2 | 1.3 |
| C18:1 | 29.9 | 29.2 | 31.3 |
| C18:2 | 9.4 | 8.0 | 12.3 |
| C18:3 | 3.9 | 3.5 | 4.8 |
| C9, t11 CLA | 4.8 | 5.1 | 4.3 |
| t10, c12 CLA | 4.7 | 5.1 | 4.0 |
| Sample from Example 3 | | | |
| C8 | 20.5 | 21.0 | 19.5 |
| C10 | 9.2 | 9.0 | 9.7 |
| C16:0 | 3.0 | 3.4 | 2.4 |
| C18:0 | 1.3 | 1.5 | 1.0 |
| C18:1 | 38.5 | 39.6 | 36.1 |
| C18:2 | 12.6 | 11.1 | 15.6 |
| C18:3 | 5.5 | 4.7 | 7.1 |
| C9, t11 CLA | 4.7 | 4.9 | 4.4 |
| t10, c12 CLA | 4.6 | 4.9 | 4.1 |
| Sample from Example 5 | | | |
| C8 | 27.2 | 29.7 | 22.1 |
| C10 | 13.8 | 13.6 | 14.1 |
| C16:0 | 2.5 | 2.6 | 2.3 |
| C18:0 | 1.2 | 1.3 | 1.1 |
| C18:1 | 31.7 | 30.5 | 34.0 |
| C18:2 | 10.3 | 8.4 | 14.0 |
| C18:3 | 4.3 | 3.5 | 5.8 |
| C9, t11 CLA | 4.6 | 5.2 | 3.5 |
| t10, c12 CLA | 4.5 | 5.2 | 3.1 |
| Sample from Example 6 | | | |
| C8 | 27.5 | 27.9 | 26.7 |
| C10 | 13.8 | 13.0 | 15.4 |
| C16:0 | 2.5 | 2.7 | 2.1 |
| C18:0 | 1.2 | 1.4 | 1.0 |
| C18:1 | 31.6 | 31.9 | 30.9 |
| C18:2 | 10.3 | 8.9 | 13.1 |
| C18:3 | 4.1 | 3.9 | 4.5 |
| C9, t11 CLA | 4.5 | 5.2 | 3.1 |
| t10, c12 CLA | 4.5 | 5.2 | 3.1 |
| Sample from Example 8 | | | |
| C8 | 16.9 | 23.9 | 2.9 |
| C10 | 8.4 | 10.9 | 3.5 |
| C16:0 | 2.4 | 2.8 | 1.5 |
| C18:0 | 1.3 | 1.4 | 1.2 |
| C18:1 | 38.6 | 35.0 | 45.7 |
| C18:2 | 15.0 | 10.2 | 24.5 |
| C18:3 | 6.3 | 4.4 | 10.1 |
| C9, t11 CLA | 5.5 | 5.6 | 5.3 |
| t10, c12 CLA | 5.6 | 5.8 | 5.3 |

The Examples show that the regiostructure of the rapeseed oil used remains partially intact; polyunsaturated fatty acids are found preferentially in the 2 position. The sample from Example 8 shows an ABA-type structure with medium-chain fatty acids in the 1,3 position and long-chain fatty acids in the 2 position.

Example 14

Comparison of the Content of Trans Fatty Acids in the Structured Lipids

The distilled lipids from Examples 2, 3, 5, 6 and 8 were analyzed for their content of trans fatty acids in comparison with the rapeseed oil used. The analysis was carried out by gas chromatography after methylation of the lipids. Conjugated trans compounds (CLA) were not included in the evaluation. The results are set out in Table 19 as % area (GC).

TABLE 19L

| | Composition of the reaction product | | | | |
|---|---|---|---|---|---|
| Fatty acid | Ex. 2 | Ex. 3 | Ex. 5 | Ex. 6 | Ex. 8 | Rapeseed oil |
| 18:1 trans | <0.1 | <0.1 | <0.1 | <0.1 | <0.1 | <0.1 |
| 18:2 trans | <0.3 | <0.3 | <0.3 | <0.3 | <0.3 | 0.3 |
| 18:3 trans | <0.5 | <0.8 | <0.7 | <0.7 | <1.0 | <1.3 |
| Total | 0.6 | 1.0 | 0.8 | 0.8 | 1.1 | 1.5 |

The Examples show that no additional unwanted trans fatty acids are formed during the enzymatic reaction and working up. The trans contents analyzed in the products emanate from the starting product used, rapeseed oil. Accordingly, the samples only contain the nutrition-physiologically positive conjugated linoleic acids.

Example 15

Comparison of the Oxidation Stabilities of the Structured Lipids

The distilled lipids from Examples 2, 3, 5, 6 and 8 were analyzed for their oxidation stability. To this end, analyses were conducted in a Metrohm Rancimat at 100° C. The distilled lipids were stabilized both with and without antioxidant (Covi-ox T 90) and analyzed by comparison with MCT, CLA triglyceride and rapeseed oil. Rapeseed oil contains natural antioxidants with a positive effect on oxidation stability. The results are set out in Table 20.

TABLE 20

| | Oxidation stability [h] | |
|---|---|---|
| Sample from | Without antioxidant | With antioxidant |
| Example 3 | 3 | 11 |
| Example 4 | 3 | 13 |
| Example 5 | 6 | 16 |
| Example 6 | 6 | 9 |
| Example 8 | 2 | 4 |
| Rapeseed oil | 12 | |
| MCT | >100 | |
| CLA triglyceride | | 6 |

The Examples show that the structured lipids treated with the antioxidant are comparable in stability with the rapeseed oil and have better stability than the CLA triglyceride.

Example 16

Comparison of the Physical Properties of Viscosity and Cloud Point of the Structured Lipids The distilled lipids from Examples 2, 3, 5, 6 and 8 were analyzed for their physical properties. To this end, their cloud point was analyzed to ASTM D2500 using an ATPEM V4701. The viscosities were rheometrically recorded at various temperatures. All measurements were carried out in comparison with rapeseed oil, MCT and CLA triglyceride. The results are set out in Table 21.

TABLE 21

| | Cloud point and viscosity | | | | |
|---|---|---|---|---|---|
| | Cloud point | Viscosity [mm/s] of | | | |
| Sample from | [° C.] | 10° C. | 20° C. | 50° C. | 70° C. |
| Example 2 | −20 | 84 | 35 | 17 | 10 |
| Example 3 | −26 | 99 | 49 | 20 | 12 |
| Example 5 | −17 | 88 | 36 | 18 | 11 |
| Example 6 | −17 | 90 | 37 | 18 | 11 |
| Example 8 | −30 | | | | |
| Rapeseed oil | −33 | 130 | 53 | 26 | 15 |
| MCT | −59 | 47 | 20 | 10 | 6 |
| CLA-TG | | 281 | 96 | 42 | 22 |

As the Examples show, the cloud point of the structured lipids is of the same order as that of rapeseed oil and other edible oils. The viscosity of the structured lipids is also of the same order as the viscosity of rapeseed oil.

Example 17

Incorporation of the Structured Lipids in Milk

The samples from Examples 3 and 5 were incorporated in milk in different concentrations. Quantities of 1% by weight and 4% by weight of the samples were added to milk with a percentage fat content of 1.5% by weight and the resulting mixture was homogenized with an Ultra-Turrax for 30 seconds at 9500 r.p.m. A white, stable and homogeneous milk was obtained in both cases.

Example 18

Incorporation of the Structured Lipids in Mayonnaise

The samples from Examples 3 and 5 were incorporated in mayonnaise in a quantity of 6% by weight. To this end, 17.8% by weight water was stirred with 2% by weight Lamegin® ZE 609 Pastille at 65° C. to form a paste. 19% by weight sunflower oil and 6% by weight of the structured lipids were heated to 40° C. and added to the emulsifier/water paste. The water phase consisting of 4% by weight vinegar (5% by volume), 50% by weight water, 0.5% by weight Prinza® 452 and 0.7% by weight sodium chloride was then heated to 65° C. and added with stirring to the oil phase. The mayonnaise was cooled with stirring to room temperature. A white stable mayonnaise formulation was obtained in both cases.

Example 19

Smoking of the Structured Lipids on Heating

Smoke point determination was carried out with the samples from Examples 3 and 5 in comparison with mixtures of rapeseed oil and MCT. The results are set out in Table 22 and represent averages of two measurements.

TABLE 22

Smoke points

| Sample from | Medium-chain fatty acids [% by weight] | Smoke point [° C.] |
|---|---|---|
| Example 3 | 29.7 | 169 |
| Example 5 | 40.0 | 171 |
| 100% rapeseed oil | 0 | 180 |
| 90% rapeseed oil + 10% MCT | 10 | 170 |
| 80% rapeseed oil + 20% MCT | 40 | 163 |
| 60% rapeseed oil + 40% MCT | 60 | 160 |
| 20% rapeseed oil + 80% MCT | 80 | 156 |
| 100% MCT | 100 | 152 |

The Examples show that the structured lipids exhibit distinctly better smoke behavior than mixtures containing MCT and rapeseed oil in corresponding concentrations.

Example 20

Production of Structured Lipids by Enzymatic Transesterification; Product Purification by Distillation 500 g MCT (Delios® V), 100 g CLA triglyceride (Tonalin TG 80) and 400 g rapeseed oil (fully degummed oil) and 0.5 g Covi-ox® T-90 were introduced into a double-jacketed reactor. 100 g immobilized *Thermomyces lanugenosus* lipase were added to the mixture and the enzyme was dried with stirring for 3 hours at 45° C. in a vacuum of 20 mbar. The immobilized enzyme was then filtered off and returned to the reactor. 1,000 g MCT (Delios® V), 200 g CLA triglyceride (Tonalin® TG 80) and 800 g rapeseed oil (fully degummed oil) and 1.0 g Covi-ox® T-90 were added and the mixture was blanketed with nitrogen and then incubated with stirring for 24 h at 45° C. After 24 h, the enzyme was removed from the crude product by filtration. The crude product was purified by short-path distillation at 205° C. in a vacuum of 0.3 mbar. The bottom product was analyzed by gas chromatography and by wet chemical analysis. The distribution of the glycerides and the fatty acid spectrum were analyzed and the oleochemical data were determined. The results are set out in Table 23. In addition, the product was deodorized with carrier gas in counter current for sensory comparison.

TABLE 23

Composition of the reaction product

| Composition | Product |
|---|---|
| Glyceride distribution [% area] | |
| Free acid, total | 0.3 |
| Monoglycerides, total | <0.1 |
| Diglycerides, total | 1.0 |
| TG (3x medium-chain) | 16.1 |
| TG (2x medium, 1x long-chain) | 47.7 |
| TG (1x medium, 2x long-chain) | 30.4 |
| TG (3x long-chain) | 4.5 |
| Fatty acid spectrum [% area] | |
| C8 | 24.1 |
| C10 | 19.9 |
| C16:0 | 2.2 |
| C18:0 | 1.1 |
| C18:1 | 28.2 |
| C18:2 | 10.0 |
| C18:3 | 4.9 |
| c9, t11 CLA | 4.9 |
| t10, c12 CLA | 4.9 |
| Wet chemical data | |
| Acid value | 0.1 |
| Hydroxyl value | 4.3 |
| Iodine value | 67 |
| Saponification value | 256 |
| Peroxide value | 2.3 |

The Example shows that high-quality structured lipids can be produced by enzymatic transesterification with pre-dried enzyme in an inert gas atmosphere and purification by distillation.

Example 21

Smoking and Oxidation Stability of the Structured Lipid from Example 20

Smoke point determination in comparison with the raw materials used and determination of oxidation stability at 100° C. in comparison with the rapeseed oil and Tonalin® TG 80 were carried out with the sample from Example 20. The results are set out in Table 24.

TABLE 24

Oxidation stability and smoke point

| Sample from | Oxidation stability [h] | Smoke point [° C.] |
|---|---|---|
| Example 20 | 20 | 187 |
| Tonalin ® TG 20 | 6 | 185 |
| Delios ® V | | 149 |
| Rapeseed oil, fully degummed | 8 | 191 |

The Examples show that the structured lipid has a distinctly better oxidation stability than the educts Tonalin® TG 80 and rapeseed oil and that its smoke behavior is comparable with that of the purely long-chain triglycerides and distinctly better than that of the medium-chain Delios® V. Comparison with the mixtures from Example 19 containing MCT and rapeseed oil in corresponding concentrations shows that the smoke behavior of the structured lipid is improved by about 25° C.

Example 22

Comparison of the Sensory Properties Against Rapeseed Oil

The sample from Example 20 (deodorized and non-deodorized) was sensorially evaluated for odor and taste in comparison with the rapeseed oil used in the synthesis. For evaluation, the parameters rancid odor, foreign odor, rancid taste, off-taste and bitterness were analyzed by a panel of 3 trained examiners. The structured lipids fared far better than rapeseed oil in the rancid odor, rancid taste and off-taste categories. In the foreign odor and bitterness categories, similar test results were obtained for the structured lipids and the rapeseed oil with a marginally better evaluation for the structured lipids. The deodorized structured lipid produced a marginally better evaluation than the non-deodorized product.

Example 23

Comparison of the Sensory Properties Against Rapeseed Oil in Milk

The sample from Example 20 (deodorized and non-deodorized) was sensorially analyzed for odor and taste in milk in comparison with the rapeseed oil used in the synthesis. For evaluation, the parameters rancid odor, foreign odor, rancid taste, off-taste, fishy taste note and bitterness were analyzed by a panel of 3 trained examiners. To this end, the samples and rapeseed oil were incorporated in milk in different concentrations. Quantities of 1% by weight, 4% by weight and 8% by weight of the samples were added to milk with a percentage fat content of 1.5% by weight and the mixture was homogenized with an Ultra-Turrax for 30 seconds at 9,500 r.p.m. A white, stable and homogeneous milk was obtained. The structured lipids incorporated in the milk fared far better than rapeseed oil in the foreign odor, off-taste and fishy taste note categories. In the other categories, similar test results were obtained for the structured lipids and the rapeseed oil with a marginally better evaluation for the structured lipids. The deodorized structured lipid produced a slightly better evaluation than the non-deodorized product.

Example 24

Comparison of the Sensory Properties Against Rapeseed Oil in Mayonnaise

The sample from Example 20 (deodorized and non-deodorized) was sensorially analyzed for odor and taste in mayonnaise in comparison with the rapeseed oil used in the synthesis. For evaluation, the parameters rancid odor, foreign odor, rancid taste, off-taste, fishy taste note and bitterness were analyzed by a panel of 3 trained examiners. To this end, the samples and rapeseed oil were incorporated in mayonnaise in a concentration of 6% by weight. To this end, 17.8% by weight water was stirred with 2% by weight Lamegin® ZE 609 Pastille at 65° C. to form a paste. 19% by weight sunflower oil and 6% by weight of the structured lipids were heated to 40° C. and added to the emulsifier/water paste. The water phase consisting of 4% by weight vinegar (5% by volume), 50% by weight water, 0.5% by weight Prinza® 452 and 0.7% by weight sodium chloride was then heated to 65° C. and added with stirring to the oil phase. The mayonnaise was cooled with stirring to room temperature. A white stable mayonnaise formulation was obtained in both cases. The structured lipids incorporated in the mayonnaise fared comparably with the rapeseed oil used in all categories.

Example 25

Comparison of the Degradation Rate in Simulated Intestinal Fluid

The samples from Examples 2 and 5 were analyzed against a mixture of triglycerides for hydrolyzability and CLA release rate in simulated intestinal fluid. To this end, a simulated intestinal fluid was prepared. Solution A: 38 ml 0.2 M NaOH and 70 ml dist. water were added to 1.36 g potassium hydrogen phosphate. Solution B: 0.5 g pancreatin was stirred with water to form a lump-free paste. Water was added while mixing in a total quantity of 30 ml. Solution C: solution A and solution B were combined. 50 mg taurocholic acid were added with stirring and the pH was adjusted to 7.5 with 0.2 M NaOH. The solution was then made up to 180 ml with dist. water.

2 g samples of the structured lipids of Examples 2 and 5 and 2 g of a lipid mixture consisting of 0.2 g CLA triglyceride (Tonalin TG 80), 0.8 g MCT and 1 g rapeseed oil were added as double determination to 40 ml preheated solution C and incubated while shaking at 37° C. After 1 h and 3h, 2 ml samples were taken and extracted for 10 mins. while shaking with 0.1 ml 1 M HCl and 0.4 ml octanol. The lipid-containing octanol phase was removed. 200 µl of the octanol phase were silylated for 30 mins. at 80° C. with 800 µl BSTFA/MSTFA and analyzed by gas chromatography. The fatty acids released were evaluated on the basis of their area based on the content of all lipid constituents (triglycerides, partial glycerides and fatty acids). The results are set out in Table 25. The values for the comparison lipid mixture are average values of the double determination.

TABLE 25

Fatty acid release during hydrolysis in simulated intestinal fluid

| | Fatty acid content after 1 h | Fatty acid content after 3 h |
|---|---|---|
| Sample from Example 2 | | |
| Medium-chain FA | 4.9% | 14.1% |
| Long-chain FA | 9.2% | 18.5% |
| CLA | 1.2% | 2.6% |
| Total | 15.3% | 35.2% |
| Sample from Example 5 | | |
| Medium-chain FA | 4.0% | 13.2% |
| Long-chain FA | 6.7% | 12.5% |
| CLA | 1.2% | 2.5% |
| Total | 11.9% | 28.2% |
| Lipid mixture of 10% GLA-TG, 40% MCT and 50% rapeseed oil | | |
| Medium-chain FA | 2.6% | 15.0% |
| Long-chain FA | 2.0% | 6.2% |
| CLA | 0.4% | 1.2% |
| Total | 5.0% | 22.4% |

The Examples show that, overall, the structured lipids are hydrolyzed far more quickly than a comparison mixture of non-structured lipids. The long-chain fatty acids in particular are released distinctly more quickly than from the comparison mixture. This means that better availability of the essential fatty acids is guaranteed and the CLA can develop its effect more quickly.

What is claimed is:

1. A process for the production of structured lipid mixtures corresponding to formula (1):

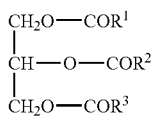 (I)

in which $R^1CO$, $R^2CO$ and $R^3CO$, independently of one another, are selected from the group consisting of
 (i) a linear saturated acyl group containing 6 to 12 carbon atoms,
 (ii) an acyl group of conjugated linoleic acid (CLA),
 (iii) an acyl group of an omega-3 fatty acid (OF), and
 (iv) an acyl group of an omega-6 fatty acid (OF),
with the proviso that the quantity of CLA acyl groups amounts to 3 to 50 mol-% and/or the quantity of OF acyl groups amounts to 5 to 25 mol-%, based on the quantity of acyl groups, said process comprising subjecting a reaction mixture of components (a) and (b) to transesterification in the presence of one or more microbial lipases and also in the presence of one or more vegetable, marine or microbial oils or mixtures thereof, wherein components (a) and (b) are:
 (a) a medium-chain triglyceride (MCTs) corresponding to formula (II):

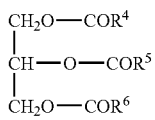 (II)

where $R^4CO$, $R^5CO$ and $R^6CO$, independently of one another, stand for a linear saturated acyl group containing 6 to 12 carbon atoms, and
 (b) a conjugated linoleic acid (CLA), an omega-3 fatty acid (OF), an omega-6 fatty acid (OF), a triglyceride based on conjugated linoleic acid (TG-CLA), an omega-3 (TG-OF) or an omega-6 fatty acid (TG-OF), and a mixture thereof,
wherein component (a) and component (b), respectively, are present in the reaction mixture in a molar ratio of 1:1 to 20:1, based on fatty acid equivalents.

2. The process according to claim 1, wherein the quantity of CLA acyl groups amounts to 5 to 15 mol-% and/or the quantity of OF acyl groups amounts to 7 to 15 mol-%, based on the quantity of acyl groups.

3. The process according to claim 1, wherein the acyl group of CLA contains at least 30% by weight t10, c12 isomers, at least 30% by weight c9, t11 isomers and less than 1% by weight 8, 10-, 11, 13- and t,t-isomers, or consists purely of c10, t12 or t9, c11 isomers.

4. The process according to claim 1, wherein the MCT and the oils are present in the reaction mixture in a molar ratio of 5:1 to 1:5, based on fatty acid equivalents.

5. The process according to claim 1, wherein the one or more microbial lipases are selected from the group consisting of *Rhizomucor, Rhizopus, Thermomyces, Pseudomonas* and *Candida*.

6. The process according to claim 5, wherein the one or more microbial lipases are selected from the group consisting of *Rhizomucor miehel* and *Thermomyces lanugenosus*.

7. The process according to claim 1, wherein at least one of the microbial lipases is immobilized.

8. The process according to claim 1, wherein the one or more vegetable, marine or microbial oils are selected from the group consisting of rapeseed oil, soybean oil, sunflower oil, thistle oil, olive oil, tuna oil, sardine oil, salmon oil, mackerel oil, algal oils, and microbial oils rich in polyunsaturated fatty acids.

9. The process according to claim 5, wherein the one or more vegetable oils are selected from the group consisting of rapeseed oil, soybean oil, and sunflower oil.

10. The process according to claim 1, further comprising the step of distilling at least a portion of unreacted fatty acids, esters and monoglycerides from the reaction products by distillation, at temperatures below 220° C. and under pressures of less than 1 mbar.

11. A process for the production of structured lipid mixtures corresponding to formula (I):

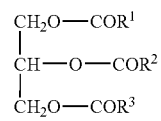 (I)

in which $R^1CO$, $R^2CO$ and $R^3CO$, independently of one another, are selected from the group consisting of
 (i) a linear saturated acyl group containing 6 to 12 carbon atoms,
 (ii) an acyl group of conjugated linoleic acid (CLA),
 (iii) an acyl group of an omega-3 fatty acid (OF), and
 (iv) an acyl group of an omega-6 fatty acid (OF),
with the proviso that the quantity of CLA acyl groups amounts to 3 to 50 mol-% and/or the quantity of OF acyl groups amounts to 5 to 25 mol-%, based on the quantity of acyl groups,
said process comprising subjecting a reaction mixture of components (a) and (b) to esterification or transesterification in the presence of (i) glycerol, (ii) one or more microbial lipases and (iii) one or more vegetable, marine or microbial oils or mixtures thereof, wherein components (a) and (b) are:
 (a) mixtures of fatty acids or esters of fatty acids corresponding to formula (III):

$R^7COOR^8$ (III)

in which $R^7CO$ is a linear saturated acyl group containing 6 to 12 carbon atoms and $R^8$ is hydrogen or an alkyl group containing 1 to 4 carbon atoms, and, optionally, glycerol, and
 (b) conjugated linoleic acid (CLA) and/or omega-3 and/or omega-6 fatty acids, wherein component (a) and component (b) or their triglycerides are present in the reaction mixture in a molar ratio of 1:1 to 20:1, based on fatty acid equivalents.

12. The process according to claim 11, wherein the quantity of CLA acyl groups amounts to 5 to 15 mol-% and/or the quantity of OF acyl groups amounts to 7 to 15 mol-%, based on the quantity of acyl groups.

13. The process according to claim 11, wherein the acyl group of the CLA, contains at least 30% by weight t10, c12 isomers, at least 30% by weight c9, t11 isomers and, in all, less than 1% by weight 8,10-, 11,13- and t,t-isomers, or consists essentially of c10, t12 or t9, c11 isomers.

14. The process according to claim 11, wherein components (a) and (b) and the oils are present in the reaction mixture in a molar ratio of 5:1 to 1:5, based on fatty acid equivalents.

15. The process according to claim 11, wherein the one or more microbial lipases are selected from the group consisting of microbial lipases selected from the group consisting of *Rhizomucor, Rhizopus, Thermomyces, Pseudomonas* and *Candida*.

16. The process according to claim 15, wherein the one or more microbial lipases are selected from the group consisting of *Candida antarctica B, Rhizomucor miehel* and *Thermomyces lanugenosus*.

17. The process according to claim 11, wherein at least one of the microbial lipases is immobilized.

18. The process according to claim 11, wherein the one or more vegetable, marine or microbial oils are selected from the group consisting of rapeseed oil, soybean oil, sunflower oil, thistle oil, olive oil, tuna oil, sardine oil, salmon oil, mackerel oil, algal oils, and other microbial oils rich in polyunsaturated fatty acids.

19. The process according to claim 18, wherein the one or more vegetable oils is rapeseed oil.

20. The process according to claim 11, wherein the product of a first esterification or transesterification is subjected to a further transesterification.

21. The process according to claim 11 further comprising the step of distilling at least a portion of unreacted fatty acids, esters and monoglycerides from the reaction products by distillation, at temperatures below 220° C. and under pressures of less than 1 mbar.

* * * * *